(12) United States Patent
Kobayashi et al.

(10) Patent No.: US 8,854,444 B2
(45) Date of Patent: Oct. 7, 2014

(54) INFORMATION PROCESSING APPARATUS AND CAPSULE ENDOSCOPE SYSTEM

(75) Inventors: Satomi Kobayashi, Kokubunji (JP); Kei Takasugi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/433,877

(22) Filed: Mar. 29, 2012

(65) Prior Publication Data

US 2012/0242813 A1 Sep. 27, 2012

Related U.S. Application Data

(63) Continuation of application No. PCT/JP2011/064261, filed on Jun. 22, 2011.

(30) Foreign Application Priority Data

Sep. 29, 2010 (JP) .................. 2010-219802

(51) Int. Cl.
*A61B 1/00* (2006.01)
*A61B 5/06* (2006.01)
*A61B 1/04* (2006.01)

(52) U.S. Cl.
CPC . *A61B 1/041* (2013.01); *A61B 5/06* (2013.01); *A61B 1/0005* (2013.01); *A61B 1/00009* (2013.01)
USPC .......................................................... 348/65

(58) Field of Classification Search
USPC .......................................................... 348/65
See application file for complete search history.

(56) References Cited

U.S. PATENT DOCUMENTS

| 7,993,265 | B2 * | 8/2011 | Suzushima et al. | 600/170 |
| 8,298,136 | B2 * | 10/2012 | Kimura et al. | 600/117 |
| 2005/0096526 | A1 * | 5/2005 | Reinschke | 600/407 |
| 2006/0183993 | A1 | 8/2006 | Horn | |
| 2007/0230893 | A1 | 10/2007 | Meron et al. | |
| 2009/0252390 | A1 | 10/2009 | Matsuzaki et al. | |
| 2010/0034436 | A1 | 2/2010 | Kono | |

(Continued)

FOREIGN PATENT DOCUMENTS

| CN | 101800846 A | 8/2010 |
| EP | 2 181 640 A1 | 5/2010 |

(Continued)

OTHER PUBLICATIONS

European Search Report dated Jul. 24, 2012 from corresponding European Patent Application No. EP 11 82 8547.7.

(Continued)

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

An information processing apparatus includes a storage unit that stores data of the in-vivo images and information which is associated with the data of the in-vivo images and related to a position of a capsule endoscope in an inside of a subject; a positional information obtaining unit that obtains positional information of the capsule endoscope in capturing the in-vivo images based on the information related to the position; and a sequence changing unit that changes a sorting sequence of the in-vivo images based on the positional information obtained by the positional information obtaining unit.

11 Claims, 12 Drawing Sheets

(56) References Cited

U.S. PATENT DOCUMENTS

| | | | |
|---|---|---|---|
| 2010/0194992 A1* | 8/2010 | Kouno | 348/700 |
| 2010/0310239 A1 | 12/2010 | Kono | |
| 2011/0196202 A1 | 8/2011 | Kimura et al. | |
| 2011/0224490 A1 | 9/2011 | Kimura et al. | |

FOREIGN PATENT DOCUMENTS

| | | |
|---|---|---|
| JP | 2006-187611 A | 7/2006 |
| JP | 2007-519440 A | 7/2007 |
| JP | 2009-195343 A | 9/2009 |
| JP | 2009-261798 A | 11/2009 |
| JP | 2010-069208 A | 4/2010 |
| JP | 2010-099137 A | 5/2010 |
| JP | 2010-142375 A | 7/2010 |
| JP | 2010-158308 A | 7/2010 |
| WO | WO 2008/041401 A1 | 4/2008 |
| WO | WO 2010/122823 A1 | 10/2010 |

OTHER PUBLICATIONS

Decision of a Patent Grant issued Mar. 6, 2012 in corresponding Japanese Patent Application No. JP 2011-551364, together with an English language translation.

International Search Report PCT/JP2011/064261 dated Aug. 9, 2011.

* cited by examiner

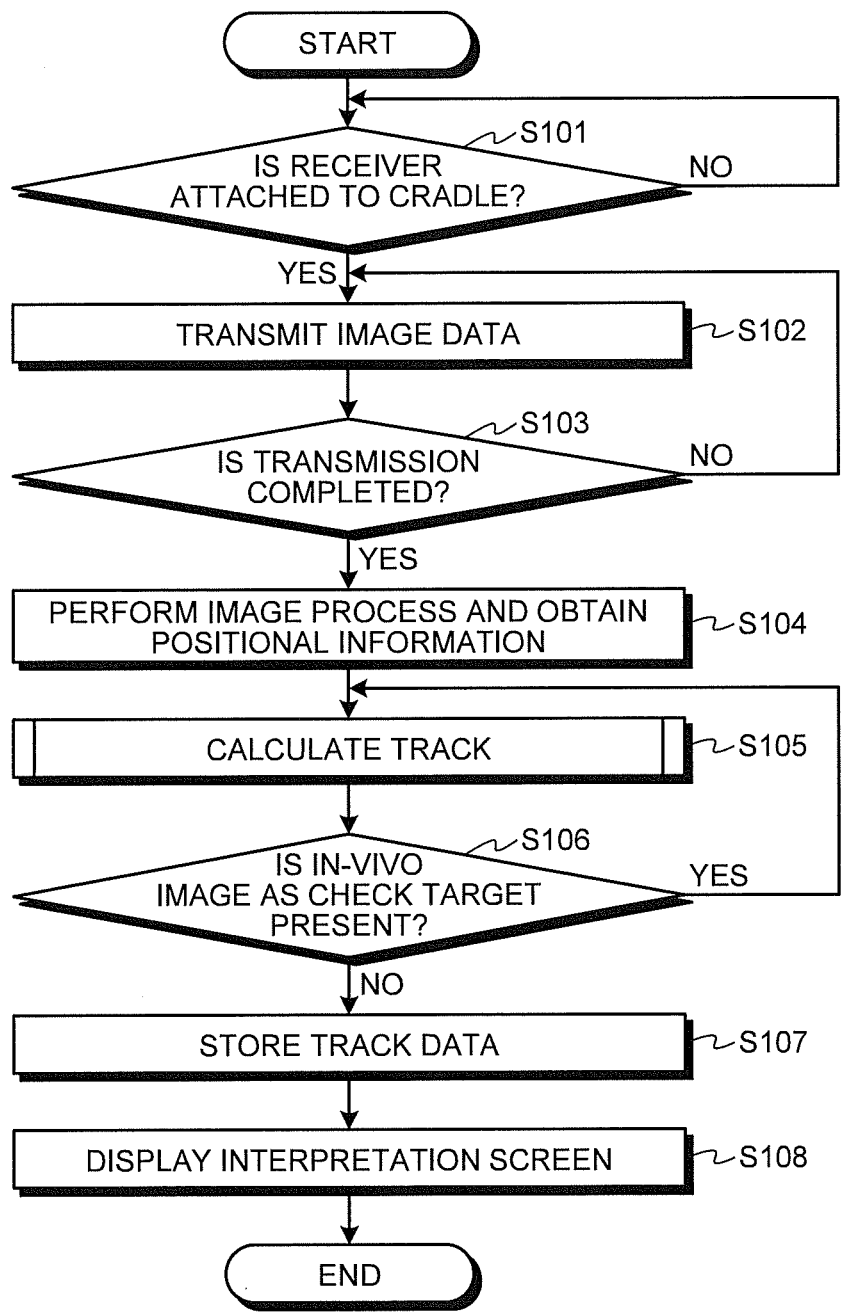

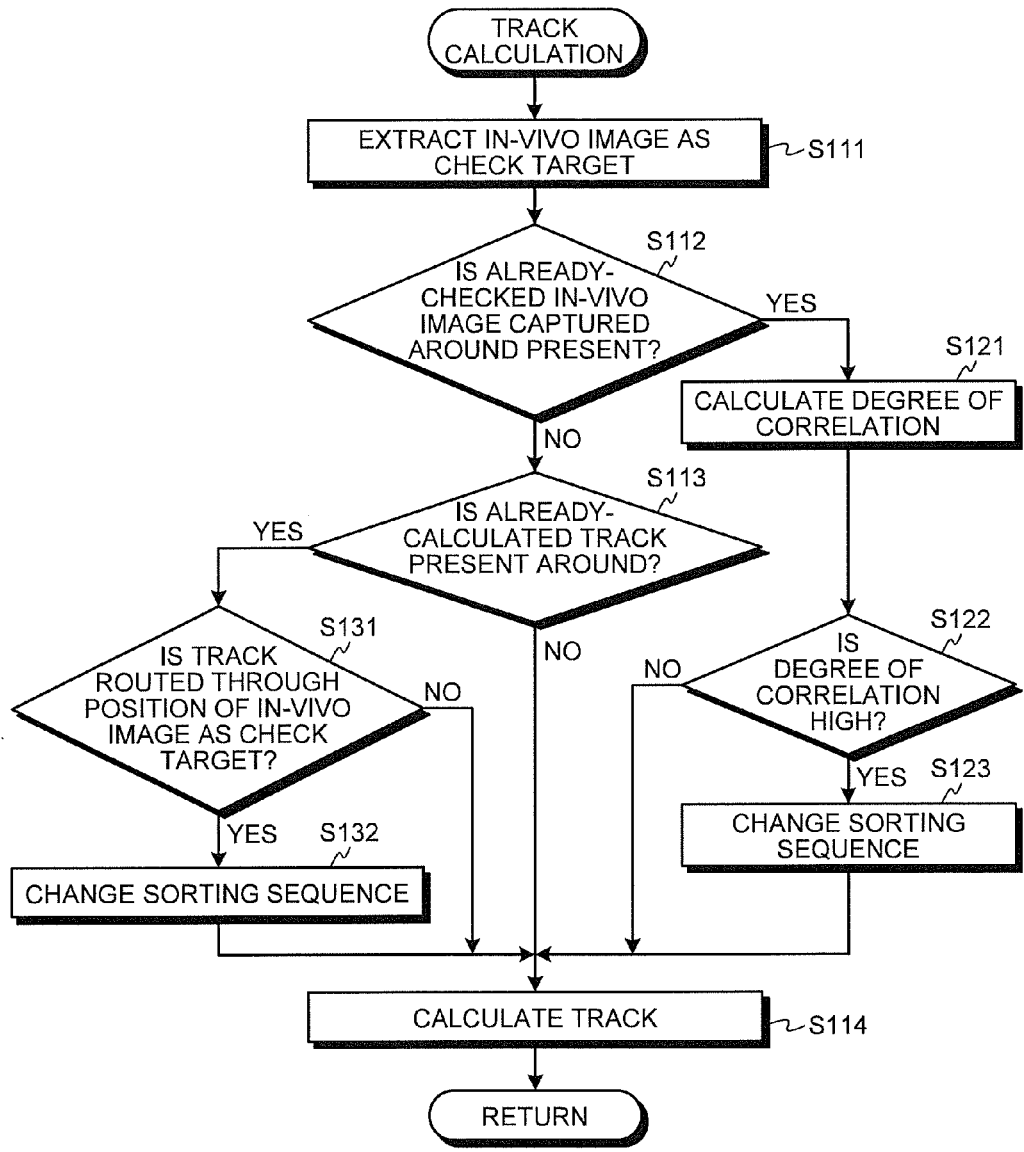

INFORMATION PROCESSING APPARATUS AND CAPSULE ENDOSCOPE SYSTEM

CROSS-REFERENCE TO RELATED APPLICATIONS

This application is a continuation of International Application No. PCT/JP2011/064261, designating the United States and filed on Jun. 22, 2011 which claims the benefit of priority of the prior Japanese Patent Application No. 2010-219802, filed on Sep. 29, 2010, and the entire contents of the International application and the Japanese Application are incorporated herein by reference.

BACKGROUND OF THE INVENTION

1. Field of the Invention

The present invention relates to an image processing apparatus that displays in-vivo images obtained by a capsule endoscope inserted to an inside of a subject and a capsule endoscope system.

2. Description of the Related Art

Conventionally, in a medical examination of a subject by using a capsule endoscope that is inserted to an inside of a subject and captures the inside of the subject, a task of observing a group of in-vivo images obtained by the capsule endoscope in a pseudo moving or in a list of still images and picking out images including a finding presenting an abnormality is performed. This task is called interpretation. Since the number of in-vivo images captured by the capsule endoscope is as many as about sixty thousands (corresponding to a time period for about eight hours), a technique of making the interpretation task more efficient by extracting an image including a predetermined feature and the like is proposed (see PCT International Patent Application Publication No. 2008/041401, for example).

When an abnormality is found, it is necessary to specify a specific position (a specific organ) of the abnormality found in the inside of the subject. Therefore, a method of specifying a position of the capsule endoscope in the inside of the subject and obtaining a track of the capsule endoscope is proposed (see Japanese Patent Application Laid-Open No. 2006-187611 and Japanese Patent Application Laid-Open No. 2010-69208, for example).

SUMMARY OF THE INVENTION

According to one aspect of the present invention, an information processing apparatus that performs an image process on data of a group of in-vivo images which are obtained from a capsule endoscope that captures in-vivo images of a subject via a receiver that performs a wireless communication with the capsule endoscope and sorted in an imaging time sequence, includes: a storage unit that stores the data of the in-vivo images and information which is associated with the data of the in-vivo images and related to a position of the capsule endoscope in an inside of the subject; a positional information obtaining unit that obtains positional information of the capsule endoscope in capturing the in-vivo images based on the information related to the position; and a sequence changing unit that changes a sorting sequence of the in-vivo images based on the positional information obtained by the positional information obtaining unit.

According to another aspect of the present invention, a capsule endoscope system includes: a capsule endoscope that is inserted to an inside of a subject, performs imaging, and generates in-vivo image data which shows in-vivo images of the subject; a receiver that receives the in-vivo image data generated by the capsule endoscope via a wireless communication; and an information processing apparatus that performs an image process on the data of a group of the in-vivo images which are obtained from the capsule endoscope via the receiver and sorted in an imaging time sequence, the information processing apparatus including a storage unit that stores the in-vivo image data and information which is associated with the in-vivo image data and related to a position of the capsule endoscope in the inside of the subject, a positional information obtaining unit that obtains positional information of the capsule endoscope in capturing the in-vivo images based on the information related to the position, and a sequence changing unit that changes a sorting sequence of the in-vivo images based on the positional information obtained by the positional information obtaining unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a flowchart showing an operation of the information processing apparatus shown in FIG. 4;

FIG. 6 is a flowchart showing a track calculating process executed by the information processing apparatus shown in FIG. 4;

DETAILED DESCRIPTION OF THE PREFERRED EMBODIMENTS

Exemplary embodiments of an information processing apparatus and a capsule endoscope system according to the present invention will be explained below with reference to the accompanying drawings. It should be noted that, while a system including a capsule endoscope that is inserted to an inside of a subject and captures in-vivo images is exemplified as an example in the explanation below, the present invention is not limited to the embodiments.

First Embodiment

Figure 1:
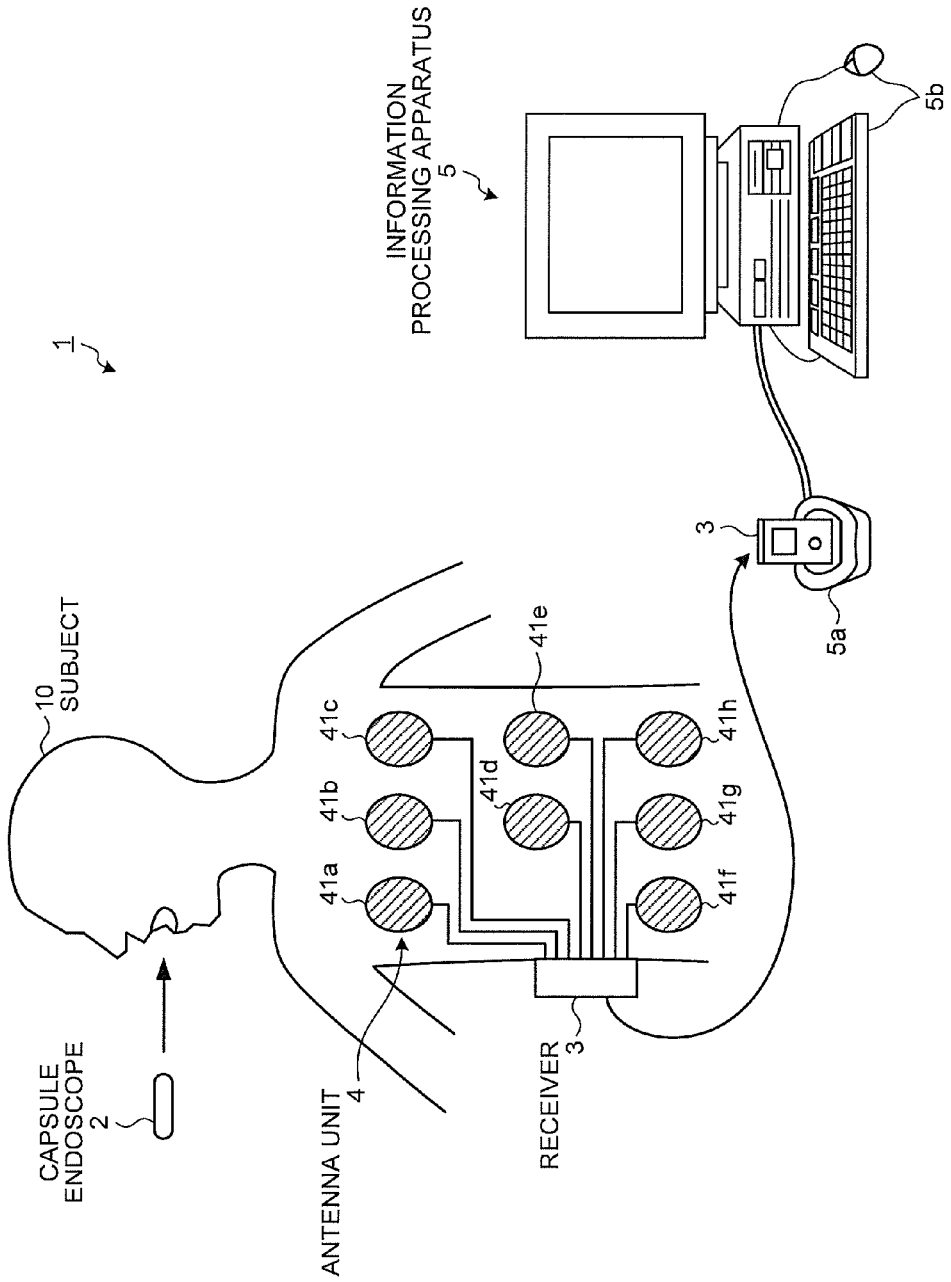
FIG. 1 is a schematic view of a configuration of a capsule endoscope system according to a first embodiment of the present invention.

FIG. 1 is a schematic view of a configuration of a capsule endoscope system according to a first embodiment of the present invention. A capsule endoscope system 1 is provided with a capsule endoscope 2 that is inserted to an inside of a subject 10, captures in-vivo images, and wirelessly transmits data of the in-vivo images to a receiver 3, the receiver 3 that receives the in-vivo image data wirelessly transmitted from the capsule endoscope 2, and an information processing apparatus 5 that displays the in-vivo images based on the in-vivo image data received by the receiver 3.

After being swallowed from a mouth of the subject 10, the capsule endoscope 2 performs a predetermined signal process with respect to imaging signals obtained by sequentially capturing images of the inside of the subject 10 at predetermined time intervals (at 0.5 second intervals, for example) while traveling an inside of organs of the subject 10 by a peristaltic motion of the organs to generate in-vivo image data. The capsule endoscope 2 wirelessly transmits the generated in-vivo image data sequentially to the receiver 3 placed outside whenever capturing in-vivo images of the subject 10. The capsule endoscope 2 is assigned with identification information (a serial number, for example) which allows the capsule endoscope to be identified and the identification information is also wirelessly transmitted together with the in-vivo image data.

The receiver 3 is provided with an antenna unit 4 including a plurality of receiving antennas 41a to 41h. The receiving antennas 41a to 41h are, for example, realized by using a loop antenna and arranged at predetermined positions on an outside surface of the subject 10 (at positions corresponding to respective organs which are along the traveling route of the capsule endoscope 2 in the inside of the subject 10, for example). The arrangement of the receiving antennas 41a to 41h may be changed arbitrarily depending on a purpose of an examination, a diagnosis, and the like. The number of antennas provided in the antenna unit 4 is not necessarily limited to eight as shown by the receiving antennas 41a to 41h and may be more or less than eight.

The receiver 3 is carried by the subject 10 and receives the in-vivo image data wirelessly transmitted from the capsule endoscope 2 via the antenna unit 4 while an imaging is performed by the capsule endoscope 2 (while the capsule endoscope 2, after inserted from a mouth of the subject 10, travels through the inside of the digestive canal until excreted, for example). The receiver 3 stores the received in-vivo image data in an embedded memory. The receiver 3 stores, by associating with the in-vivo image data, reception intensity information of each of the receiving antennas 41a to 41h at a time of the image reception and time information which indicates a reception time in the memory. The reception intensity information and the time information is used in the information processing apparatus 5 as information related to the position of the capsule endoscope 2. After the imaging by the capsule endoscope 2 is finished, the receiver 3 is detached from the subject 10 and connected to the information processing apparatus 5 for the purpose of transferring (downloading) information including the in-vivo image data.

The information processing apparatus 5 is realized by a workstation or a personal computer provided with a display unit such as a CRT display device and a liquid crystal display device, performs a predetermined process on the in-vivo image obtained via the receiver 3 and position-related information, and displays the in-vivo images in the display unit. An operation inputting device 5b such as a keyset and a mouse is connected to the information processing apparatus 5. Alternatively, a touchscreen overlapped with the display unit may be provided as the operation inputting device 5b. While operating the operation inputting device 5b, a user (interpreter) observes (examines) a biological body site (the esophagus, stomach, small intestine, large intestine, and the like, for example) in the inside of the subject 10 and makes a diagnosis on the subject 10 based on the observation (examination) by interpreting the in-vivo images of the subject 10 sequentially displayed in the information processing apparatus 5.

The information processing apparatus 5 is provided with a universal serial bus (USB) port, via which a cradle 5a is connected. The cradle 5a is a reader that reads the in-vivo image data from the memory of the receiver 3. When the receiver 3 is attached to the cradle 5a, the receiver 3 is electrically connected to the information processing apparatus 5 and thereby the in-vivo image data and its associated information (reception intensity information, time information, and identification information of the capsule endoscope 2) stored in the memory of the receiver 3 is transferred to the information processing apparatus 5. The information processing apparatus 5 obtains a series of in-vivo image data concerning the subject 10 and its associated information in this manner, further performs a process to be explained later, and thus displays the in-vivo images. The information processing apparatus 5 may be connected to an output device such as a printer and may output the in-vivo images to the output device.

The image processing apparatus 5 may obtain the in-vivo image data captured by the capsule endoscope 2 in various methods other than the method explained above. For example, a memory such as a USB memory and Compact-Flash (registered trademark) which can be detachably attached to the receiver 3 may be used instead of the embedded memory in the receiver 3. In this case, after the in-vivo image data from the capsule endoscope 2 is stored in the memory, only the memory may be detached from the receiver 3 and inserted into the USB port and the like of the information processing apparatus 5, for example. Alternatively, the information processing apparatus 5 may be provided with a communication function with an external device and may obtain the in-vivo image data from the receiver 3 via a wire or wireless communication.

Figure 2:
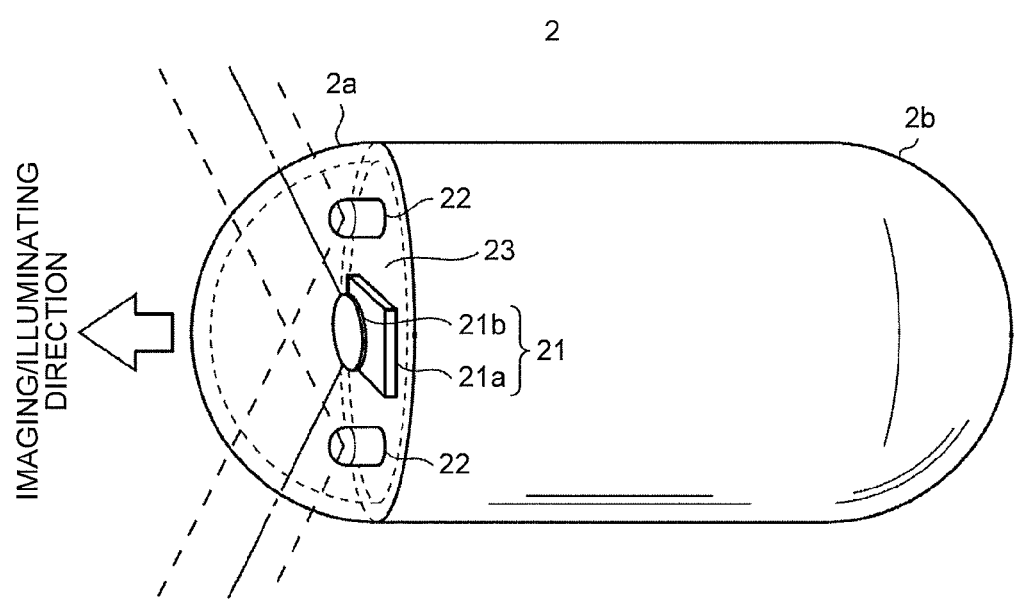
FIG. 2 is a schematic view of a configuration of the capsule endoscope shown in FIG. 1.
Figure 3:
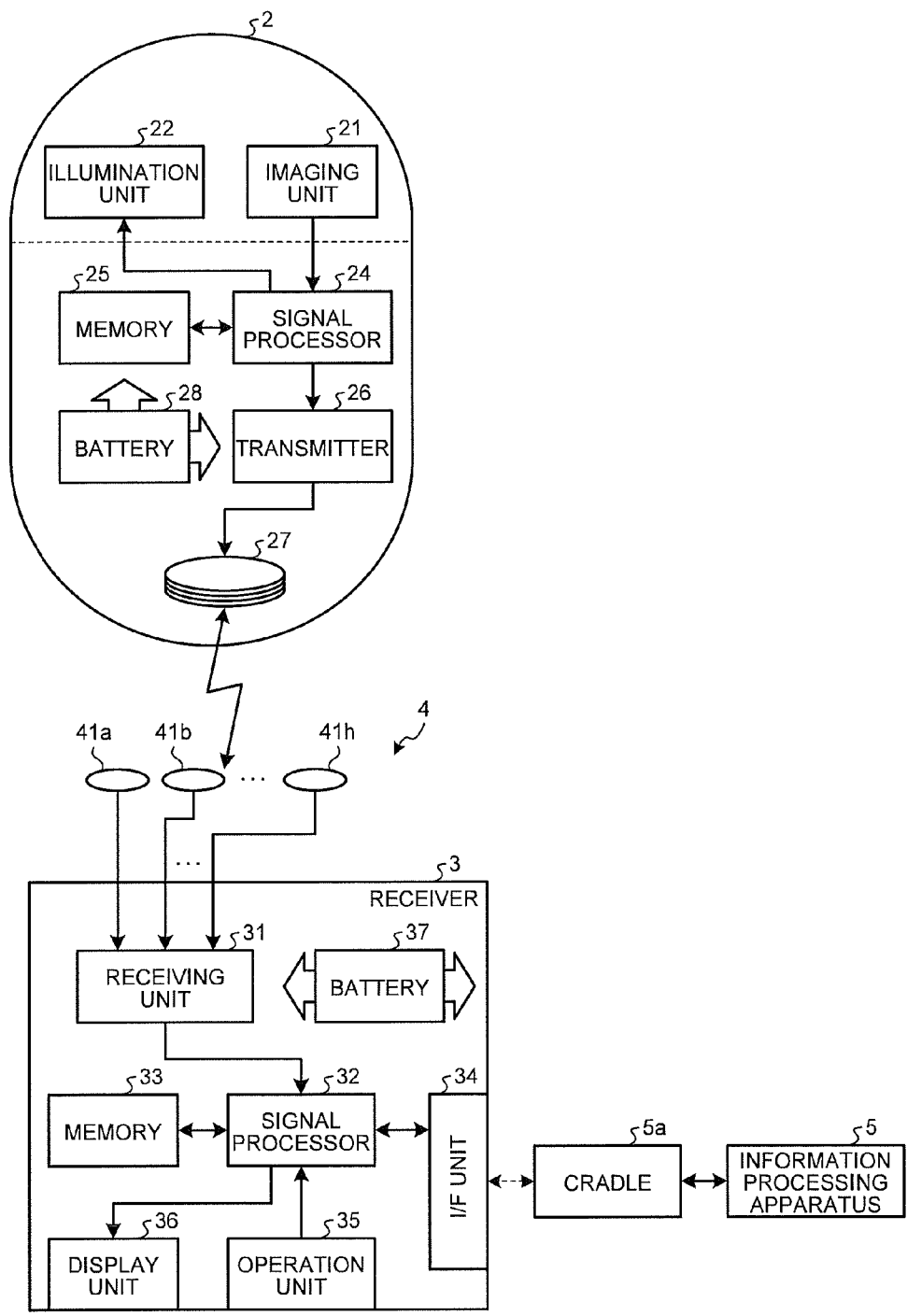
FIG. 3 is a block diagram of a configuration of the capsule endoscope and a receiver shown in FIG. 1.

Next, devices constituting the capsule endoscope system 1 will be explained in detail. FIG. 2 is a schematic view of an example of a configuration of the capsule endoscope 2. FIG. 3 is a block diagram of a configuration of the capsule endoscope 2 and the receiver 3.

As shown in FIG. 2, the capsule endoscope 2 is housed in a capsule-shaped casing (housing) formed by a casing 2b which has an approximately cylindrical shape or a semi-elliptical spherical shape and whose one end has a hemispherical dome shape and the other end has an opening; and an optical dome 2a which has a hemispherical shape and seals an inside of the casing 2b in a water-tight manner when fitted to the opening of the casing 2b. The capsule-shaped casing (2a, 2b) has a size to be swallowed by the subject 10, for example. In the present embodiment, at least the optical dome 2a is formed of a transparent material.

As shown in FIGS. 2 and 3, the capsule endoscope 2 is provided with an imaging unit 21 that captures images of the inside of the subject 10, an illumination unit 22 that illuminates the inside of the subject 10 in the imaging, a circuit board 23 on which respective driving circuits and the like for driving the imaging unit 21 and the illumination unit 22 are formed, a signal processor 24, a memory 25, a transmitter 26, an antenna 27, and a battery 28.

The imaging unit 21 includes an imaging element 21a such as a CCD and a CMOS that generate data of an in-vivo image of the subject from an optical image formed on a light reception surface and an optical system 21b such as an objective lens provided at a side of the light reception surface of the imaging element 21a, for example. The illumination unit 22 is realized by a light emitting diode (LED) and the like that emits a light towards the inside of the subject 10 in the imaging. The imaging element 21a, the optical system 21b, and the illumination unit 22 are mounted on the circuit board 23.

The driving circuit of the imaging unit 21 operates under a control of the signal processor 24 to be described later, generates an imaging signal indicating an image of the inside of the subject 10 regularly (two frames per second, for example), and inputs the generated imaging signal to the signal processor 24. The imaging unit 21 and the illumination unit 22 will be explained below on the assumption that respective driving circuits are included.

The circuit board 23 on which the imaging unit 21 and the illumination unit 22 are mounted is arranged at a side of the optical dome 2a in the inside of the capsule-shaped casing (2a, 2b) in a state where the light reception surface of the imaging element 21a and a direction of the light emission of the illumination unit 22 are oriented to the inside of the subject 10 via the optical dome 2a. Therefore, the imaging direction of the imaging unit 21 and the illuminating direction of the illumination unit 22 are oriented to an outside of the capsule endoscope 2 via the optical dome 2a as shown in FIG. 2. This configuration enables capturing images of the inside of the subject 10 by the imaging unit 21 while illuminating the inside of the subject 10 by the illumination unit 22.

The signal processor 24 controls each unit in the capsule endoscope 2, generates digital in-vivo image data via an A/D conversion of the imaging signal output from the imaging unit 21, and performs a predetermined signal process. The memory 25 temporarily stores various operations to be performed by the signal processor 24 and in-vivo image data to which the signal process is performed by the signal processor 24. The transmitter 26 and the antenna 27 superimpose the in-vivo image data stored in the memory 25 with the identification information of the capsule endoscope 2 on a wireless signal and transmit it to the outside. The battery 28 supplies an electric power to each unit in the capsule endoscope 2. Here, the battery 28 is configured to include a power source circuit that raises a voltage of an electric power supplied from a primary battery such as a button battery or a secondary battery.

The receiver 3 is provided with a receiving unit 31, a signal processor 32, a memory 33, an interface (I/F) unit 34, an operation unit 35, a display unit 36, and a battery 37. The receiving unit 31 receivers the in-vivo image data wirelessly transmitted from the capsule endoscope 2 via the receiving antennas 41a to 41h. The signal processor 32 controls each unit in the receiver 3 and performs a predetermined signal process on the in-vivo image data received by the receiving unit 31. The memory 33 stores various operations to be performed by the signal processor 32, and the in-vivo image data to which the signal process is performed by the signal processor 32 and its associated information (reception intensity information, time information, and the like). The interface unit 34 transmits the image data stored in the memory 33 to the information processing apparatus 5 through the cradle 5a. The operation unit 35 allows a user to input various operational instructions and settings to the receiver 3. The display unit 36 notifies a user of or displays information of various kinds. The battery 37 supplies an electric power to each unit in the receiver 3.

Figure 4:
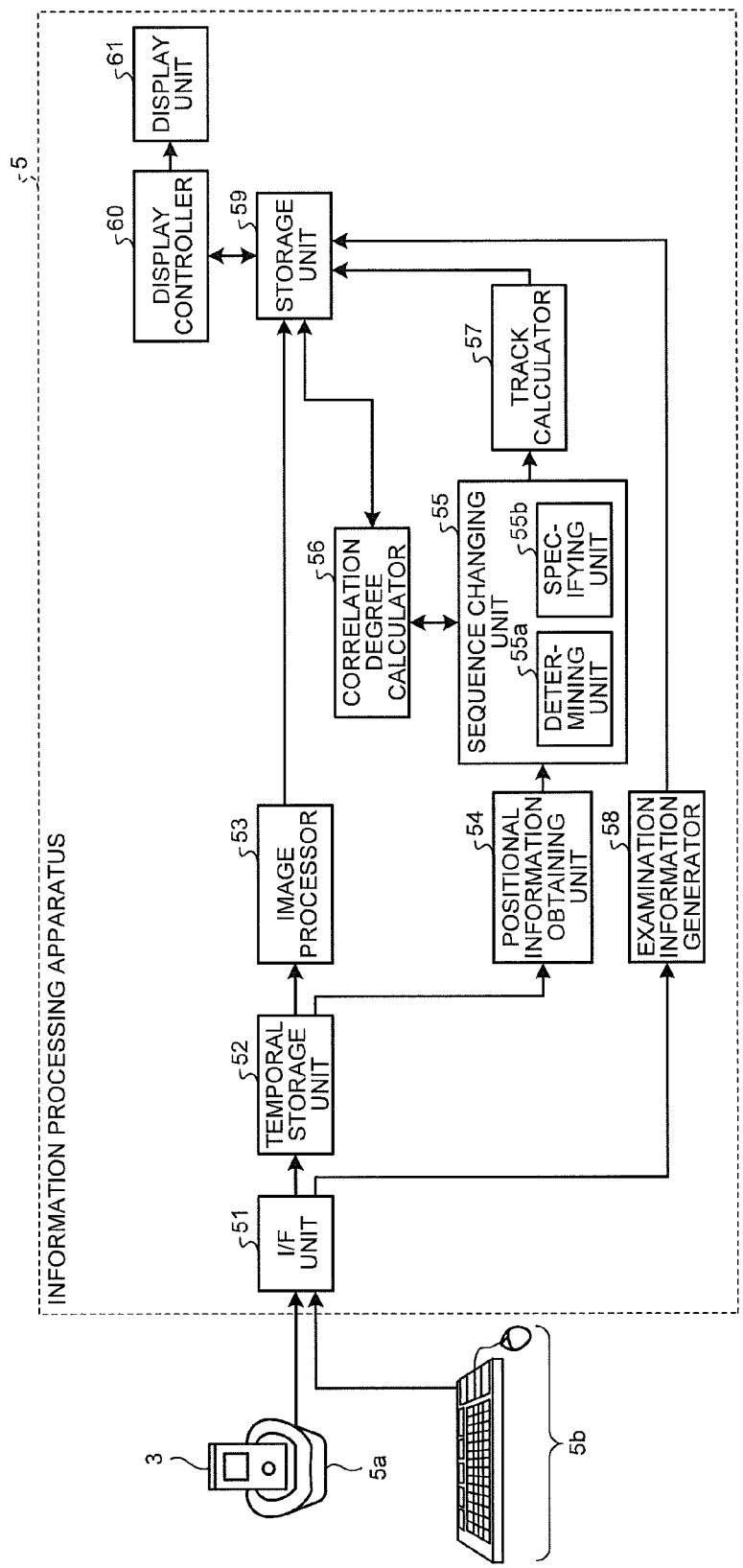
FIG. 4 is a block diagram of a configuration of the information processing apparatus shown in FIG. 1.

FIG. 4 is a block diagram of a configuration of the information processing apparatus 5. As shown in FIG. 4, the information processing apparatus 5 is provided with an interface (I/F) unit 51, a temporal storage unit 52, an image processor 53, a positional information obtaining unit 54, a sequence changing unit 55, a correlation degree calculator 56, a track calculator 57, an examination information generator 58, a storage unit 59, a display controller 60, and a display unit 61.

The interface unit 51 accepts the in-vivo image data input through the cradle 5a and its associated information, and instructions and information of various kinds input via the operation inputting device 5b.

The temporal storage unit 52 is realized by a volatile memory such as a DRAM and an SRAM, and temporarily stores the in-vivo image data and its associated information input from the receiver 3 via the interface unit 51. Alternatively, a recording medium such as a hard disk drive (HDD), a magnetooptical (MO) disk, a CD-R, and a DVD-R and a driving device that drives such a recording medium may be provided instead of the temporal storage unit 52, and the in-vivo image data input from the interface unit 51 may be temporarily stored in the recording medium.

The image processor 53 performs various kinds of image processes such as a white balance process, a demosaicing, a color conversion, a density conversion (a gamma conversion and the like), a smoothing (a noise elimination and the like), a sharpening (an edge emphasis and the like), and an image recognition with respect to the in-vivo image data stored in the temporal storage unit 52. The image recognition process specifically includes a detection of an image area having a feature of a diseased site such as neoplastic, vascular, and hemorrhagic areas, a discrimination of organs, a calculation of an average color The positional information obtaining unit 54 obtains information (positional information) which indicates a positional coordinate of the capsule endoscope 2 in the imaging of each in-vivo image by performing a position estimating process based on the reception intensity information and the time information stored in the temporal storage unit 52. Specifically, the positional information obtaining unit 54 obtains the reception intensity of each of the receiving antennas 41a to 41h from the temporal storage unit 52, the reception intensity being associated with in-vivo image data received at a given time, and extracts a spherical area whose radius is a distance depending on the reception intensity centering around each of the receiving antennas 41a to 41h. Here, the lower the reception intensity becomes, the larger the radius becomes. The position where these areas intersect is estimated to be the position of the capsule endoscope 2 at the given time, i.e., the position in the subject 10 (hereinafter referred to as "position of in-vivo image") where the in-vivo image is captured. The obtained positional information is associated with the in-vivo image and the time information and stored in the storage unit 59.

As for the specific method of the position estimating process, known various methods other than the method described above may be applied. Besides, the position estimating process is not necessarily required to be performed on all the in-vivo images in time series and may be performed through a sampling in a predetermined density.

The sequence changing unit 55 changes the sorting sequence of the in-vivo images in the initial imaging time sorting sequence based on the positional information obtained by the positional information obtaining unit 54 and the degree of correlation calculated by the correlation degree calculator 56 to be described later. Specifically, the sequence changing unit 55 changes the sequence so that the series of in-vivo images shows a stream from an upper area to a lower area in the digestive canal by extracting in-vivo images which each is a target on which whether to change the sorting sequence is determined based on the positional information and evaluating the degree of correlation in the in-vivo images according to a predetermined criterion. The sequence changing unit 55 is provided with a determining unit 55*a* that determines whether or not the capsule endoscope 2 has performed a reciprocatory motion and a specifying unit 55*b* that specifies in-vivo images which are determined to be captured redundantly when the reciprocatory motion is determined to be present by the determining unit 55*a*.

The correlation degree calculator 56 calculates the degree of correlation in the in-vivo images which are each treated as the determination target by the sequence changing unit 55.

The track calculator 57 calculates a track along which the capsule endoscope 2 has passed during a period after the capsule endoscope 2 is inserted to the inside of the subject 10 and until excreted to the outside by sequentially joining respective positional coordinates of the in-vivo images according to the sorting sequence, changed by the sequence changing unit 55, of the in-vivo images.

The examination information generator 58 generates information concerning an appropriate examination based on the information input via the operation inputting device 5*b*. Specifically, the information includes patient information (ID, name, sex, age, date of birth, and the like) for identifying the subject 10 as a patient and medical examination information (hospital name, name of a doctor or a nurse who performs an administration of a capsule endoscope, date and time of the capsule administration, date and time when data is obtained, serial number of the capsule endoscope 2, serial number of the receiver 3, and the like) for identifying the content of the medical examination for the subject 10. The examination information may be generated in advance before the transmission of the in-vivo image data from the receiver 3 or may be generated after the transmission of the in-vivo image data.

The storage unit 59 stores, in addition to the various process programs performed by the image processing apparatus 5, in-vivo image data to which an image process is performed by the image processor 53, the positional information obtained by the positional information obtaining unit 54, the track data calculated by the track calculator 57, the examination information generated by the examination information generator 58, and the like. The storage unit 59 is realized by a recording medium such as a semiconductor memory like a flash memory, a random access memory (RAM), and a read only memory (ROM), a hard disk drive (HDD), a magnetooptical (MO) disk, a CD-R, and a DVD-R and a driving device that drives the recording medium, for example.

The display controller 60 controls the display unit 61 to display an interpretation screen including the in-vivo images and the track of the capsule endoscope 2 and other information of various kinds in a predetermined format.

The display unit 61 is realized by a CRT display device and a liquid crystal display device and displays the interpretation screen including the in-vivo images of the subject 10 and information of various kinds under the control by the display controller 60.

An operation of the image processing apparatus 5 will be explained next with reference to FIG. 5. FIG. 5 is a flowchart showing an operation of the information processing apparatus 5. At step S101, when the receiver 3 is attached to the cradle 5*a* ("Yes" at step S101), the transmission of the in-vivo image data and its associated information stored in the memory 33 of the receiver 3 to the image processing apparatus 5 is started (step S102). The transmitted in-vivo image data and the like are stored in the temporal storage unit 52. When the receiver 3 is not attached to the cradle 5*a* ("No" at step S101), the information processing apparatus 5 waits for the receiver 3 to be attached.

At step S103, when the transmission of the in-vivo image data and the like is completed ("Yes" at step S103), the image processor 53 performs an image process on the in-vivo image data stored in the temporal storage unit 52 and the positional information obtaining unit 54 obtains the position of each in-vivo image based on the reception intensity information and the time information stored in the temporal storage unit 52 (step S104). The in-vivo image data to which the image process is performed and the positional information indicating the position of each in-vivo image is stored in the storage unit 59.

Next at step S105, the image processing apparatus 5 calculates a track while checking respective positional coordinates of the in-vivo images sorted in the imaging time sequence and arbitrarily changing their sorting sequence. This process is repetitively performed as far as an in-vivo image as a check target is present ("Yes" at step S106).

At step S106, when no more in-vivo image as a check target is present ("No" at step S106), the storage unit 59 stores the track data calculated by the track calculator 57 (step S107). At step S108, the display controller 60 reads out the in-vivo image data to which the image process is performed and the track data from the storage unit 59 and controls the display unit 61 to display the interpretation screen. A display example of the interpretation screen will be described later.

Figure 7A:
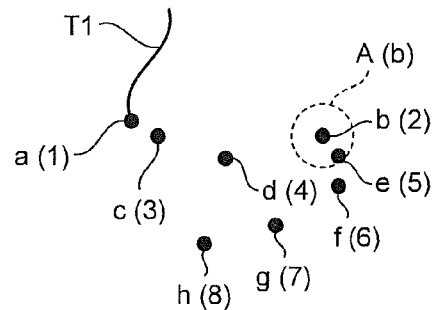
FIGS. 7A to 7E are explanatory views of the track calculating process.
Figure 7B:
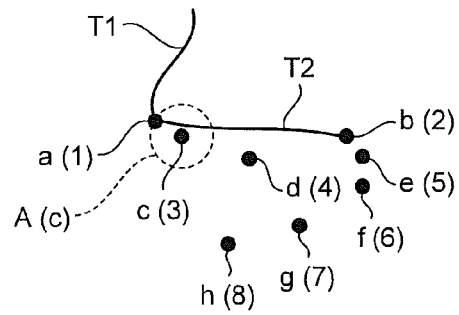
Figure 7C:
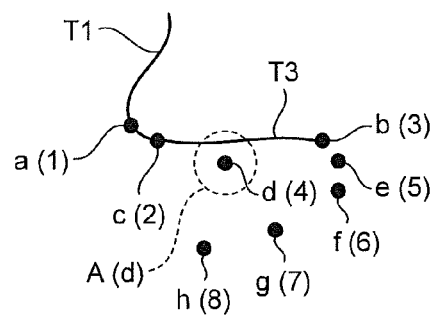
Figure 7D:
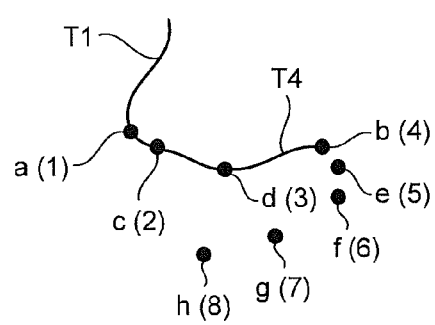
Figure 7E:
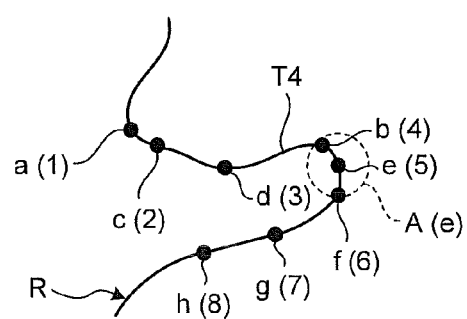

Next, a track calculating process at step S105 will be explained with reference to FIGS. 6 to 7E. FIG. 6 is a flowchart showing a track calculating process performed by the information processing apparatus 5. FIGS. 7A to 7E are explanatory views of the track calculating process. In each of FIGS. 7A to 7E, positions of in-vivo images are indicated by points a to h. Parenthetic numerals (1) to (8) provided to respective points a to h indicate the sorting sequence of the in-vivo images at the respective points a to h. Since the in-vivo images at the respective points a to h are sorted in the imaging time sequence in an initial state, the sequence of the reference symbol a to h corresponds to the sorting sequence (1) to (8) provided thereto in FIG. 7A. In FIG. 7A, a track T1 calculated on the way to the point a is shown.

First at step S111, the sequence changing unit 55 extracts an in-vivo image as a check target and obtains positional information including the positional coordinate of the in-vivo image. The order of the extraction of the check target is not specifically limited as long as all check targets are covered. The first embodiment is configured to perform the check along the initial sorting sequence from (2) to (8), starting from an in-vivo image (at the point b in the sequence 2) captured right after the in-vivo image at the point a (in the sequence 1) where the track T1 is already calculated.

At step S112, the sequence changing unit 55 checks whether or not an already-checked in-vivo image captured around the in-vivo image as the check target is present. Specifically, whether or not a positional coordinate of an already-checked in-vivo image is present within a predetermined range centering around the positional coordinate of the in-vivo image as the check target (within a cube whose side has a predetermined length or within a sphere having a predetermined radius, for example) is determined. The size of the predetermined range (the length of one side of the cube, the radius of the sphere, or the like, for example) may be determined based on an imaging frame rate and an average traveling velocity of the capsule endoscope 2, for example. Alternatively, the size of the predetermined range may be determined based on an accuracy of a positional estimation (a sampling density in which the positional estimating process is performed). For example, when the point b shown in FIG. 7A is checked, no already-checked point is present within a predetermined range A(b). When no already-checked point is present within the predetermined range of the check target point in this situation ("No" at step S112), the operation moves to step S113.

At step S113, the sequence changing unit 55 checks whether or not an already-calculated track is present around the position of the in-vivo image as the check target. Specifically, whether or not a track passes through the predetermined range of the point corresponding to the in-vivo image as the check target is determined. In the case of the point b shown in FIG. 7A for example, no track passing through the predetermined range A(b) is present. When no already-calculated track passing through the predetermined range of the check target point in this situation ("No" at step S113), the operation moves to step S114.

At step S114, the track calculator 57 calculates a track which joins the position of the in-vivo image as the check target and the position of an in-vivo image present right before the target in-vivo image. As a result, a track T2 joining the point a and the point b is generated as shown in FIG. 7B.

Next, a process in the case where an already-checked in-vivo image captured around the in-vivo image as the check target is present at step S112 ("Yes" at step S112) will be explained. For example, when the point c shown in FIG. 7B is checked, it is found that the point a is included within a predetermined range A(c).

In this case, the correlation degree calculator 56 calculates a degree of correlation between the in-vivo image as the check target and the in-vivo image whose imaging position is determined to be close (in-vivo image as a comparison target) (step S121). As the degree of correlation, known various indexes such as a correlation value in a fixed size block, a traveling amount of a template calculated via a block matching method (magnitude of a vector), and a change rate in brightness between in-vivo images may be used, for example. The larger the correlation value, between the in-vivo image as the check target and the in-vivo image as the comparison target, in a corresponding fixed size block is, the higher the degree of correlation becomes, for example. In the block matching method, the smaller a traveling amount of a template between the in-vivo image as the check target and the in-vivo image as the comparison target is, the higher the degree of correlation becomes. The lower a change rate in the brightness between the in-vivo image as the check target and the in-vivo image as the comparison target is, the higher the degree of correlation therebetween becomes.

At step S122, the determining unit 55*a* determines whether or not the degree of correlation calculated by the correlation degree calculator 56 is high, i.e., how the capsule endoscope 2 travels in the inside of the subject 10. Here, the degree of correlation between in-vivo images which are close to each other in position is considered to depend on the differences explained in (i) to (iii) below.

(i) A Situation where the Degree of Correlation Becomes Significantly High

It is considered that the degree of correlation between in-vivo images becomes significantly high when the same position is captured redundantly due to the reciprocatory motion of the capsule endoscope 2 in the inside of the subject 10, for example.

(ii) A situation where the degree of correlation becomes moderate to high

It is considered that the degree of correlation becomes moderate to high when the capsule endoscope 2 is retained and thereby the traveling distance is short while the motion of the intestine in the subject 10 is working or when the capsule endoscope 2 performs a reciprocatory motion within a certain range and thereby positions comparatively close to each other are captured, for example.

(iii) A Situation where the Degree of Correlation Becomes Low

It is determined that in-vivo images locate close to each other when positions overlap due to a tortuous shape of the intestine even though different positions in the intestine canal are captured. In this situation, the degree of correlation between the in-vivo images becomes low.

In the first embodiment, the degree of correlation between in-vivo images is determined to be high when the degree of correlation is moderate or high, i.e., in the situation (ii) described above and to be low when the degree of correlation is low, i.e., in the situation (iii) described above.

When the degree of correlation between in-vivo images is determined to be high ("Yes" at step S122), the sequence changing unit 55 changes the sorting sequence of the in-vivo images based on the positional information of the in-vivo image as the check target, the in-vivo image as the comparison target, and an in-vivo image right before or after the comparison target (step S123). On this occasion, the specifying unit 55*b* specifies the in-vivo images whose degree of correlation is high as a group of in-vivo images whose imaging positions are close to each other and sets a flag in in-vivo image data so that they can be treated as in-vivo images belonging to the same group. Alternatively, the specifying unit 55*b* may specify the in-vivo images whose degree of correlation is significantly high as a group of in-vivo images whose imaging positions are the same and set a flag in the in-vivo image data. On the other hand, when the degree of correlation between the in-vivo images is low ("No" at step S122), the original sorting sequence remains and the operation moves to step S114.

When the degree of correlation between the in-vivo image (check target) at the point c shown in FIG. 7B and the in-vivo image (comparison target) at the point a is determined to be high, it is considered that the capsule endoscope 2 has performed a reciprocatory motion around the point a in the inside of the subject 10 and the imaging is performed at the point c in the process. In this situation, the sequence changing unit 55 extracts a positional coordinate of a point right before or after the point a (the point b in the case in FIG. 7B) and changes the sorting sequence of the in-vivo images so that a route passing through these three points becomes the shortest. Thus, the initial sorting sequence "the point a(1)→the point b(2)→the point c(3)" is changed to the sequence "the point a(1)→the point c(2)→the point b(3)" as shown in FIG. 7C.

At subsequent step S114, the track calculator 57 calculates a track based on the changed sorting sequence. Thus, the track T2 joining the point a and the point b is deleted and a track T3 joining the point a, the point c, and the point b in this order is added.

Next at step S113, a process in the case where an already-calculated track is present around the position of the in-vivo image as the check target ("Yes" at step S113) will be explained. For example, when the point d shown in FIG. 7C is checked, it is found that the track T3 passes through a predetermined range A(d).

In this situation, the sequence changing unit 55 determines whether or not the detected track is routed through the position of the in-vivo image as the check target (step S131). This determination is performed by using one of the following methods (i) to (iii), for example.

(i) Determination of Degree of Similarity with Interpolated Image

Figure 8:
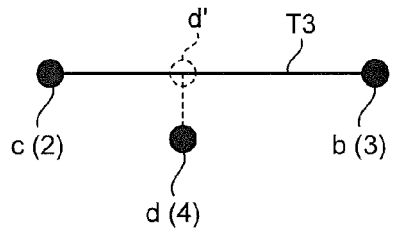
FIG. 8 is an explanatory view of a method of determining whether or not a detected track is routed through an in-vivo image as a check target.

In making a determination on the point d for example, an interpolated image is generated based on the in-vivo images at the point c and the point b which are both ends of the detected track T3. It is preferable to generate the interpolated image by taking a mutual positional relation between in-vivo images (distance and the like between in-vivo images) into consideration. For example, an interpolated image at a position d' obtained by projecting the position d onto the track T3 is generated as shown in FIG. 8. Then, a degree of similarity between the interpolated image and the in-vivo image at the point d is calculated. As the degree of similarity, various indexes such as a correlation coefficient, a change rate in brightness, and a combination thereof may be used. For example, the larger the correlation coefficient is, the higher the degree of similarity becomes. Besides, the lower the change rate in brightness is, the higher the degree of similarity becomes. When the degree of similarity is high, the track T3 is determined to be routed through the point d. On the other hand, when the degree of similarity is low, the track T3 is determined not to be routed through the point d.

(ii) Optical Flow

An optical flow indicates a travel amount expressed as vector data through an association of the same object (object position) captured at different times in two images. As a method of calculating the optical flow, known methods such as a block matching and a gradient method are used. In making a determination on the point d, respective optical flows between the point c and the point d and between the point d and the point b are calculated on the assumption that the point d locates between the point c and the point b, and whether or not the optical flows are smoothly connected to each other is determined. When the optical flows are smoothly connected to each other, the track T3 is determined to be routed through the point d. On the other hand, when the optical flows are not smoothly connected to each other, the track T3 is determined not to be routed through the point d.

(iii) Calculation of Degree of Correlation Via Block Matching

In making a determination on the point d for example, the block matching is performed between the in-vivo image at the point c and the in-vivo image at the point d and between the in-vivo image at the point d and the in-vivo image at the point b to obtain the number of matching templates. When the number of matching templates is equal to or more than a predetermined threshold each between the point c and the point d and between the point d and the point b, it is determined that the point d is highly correlated with both of the point c and the point b and the track T3 is routed through the point d. On the other hand, when the number of matching templates is less than the predetermined threshold at least one of the relations between the point c and the point d and between the point d and the point b, it is determined that the track T3 is not routed through point d. Alternatively, a summation of correlation coefficients and a maximum value of the correlation coefficients in the block matching may be obtained instead of the number of matching templates, and the values may be compared to a predetermined threshold to determine whether or not the track T3 is routed through the point d.

When the detected track is determined to be routed through the position of the in-vivo image as the check target ("Yes" at step S131), the sequence changing unit 55 changes the sorting sequence of the in-vivo images at both ends of the detected track (step S132). When the track T3 is determined to be routed through the point d, for example, the sequence changing unit 55 changes the sorting sequence of the in-vivo images to "the point c(2)→the point d(3)→the point b(4)" according to the determination. At subsequent step S114, the track calculator 57 deletes the track T3 joining the point c and the point b and adds a track T4 joining the point c, the point d, and the point b in this order (see FIG. 7D).

On the other hand, when the detected track is determined not to be routed through the in-vivo image as the check target ("No" at step S131), the original sorting sequence remains and the operation moves to step S114.

The processes shown at steps S111 to S114, S121 to S123, and S131 to S132 are further repeated with respect to points e to h while a predetermined range for each check target (a predetermined range A(e) centering around the point e, for example) is set. Thus, a total track R is generated as shown in FIG. 7E.

Figure 9:
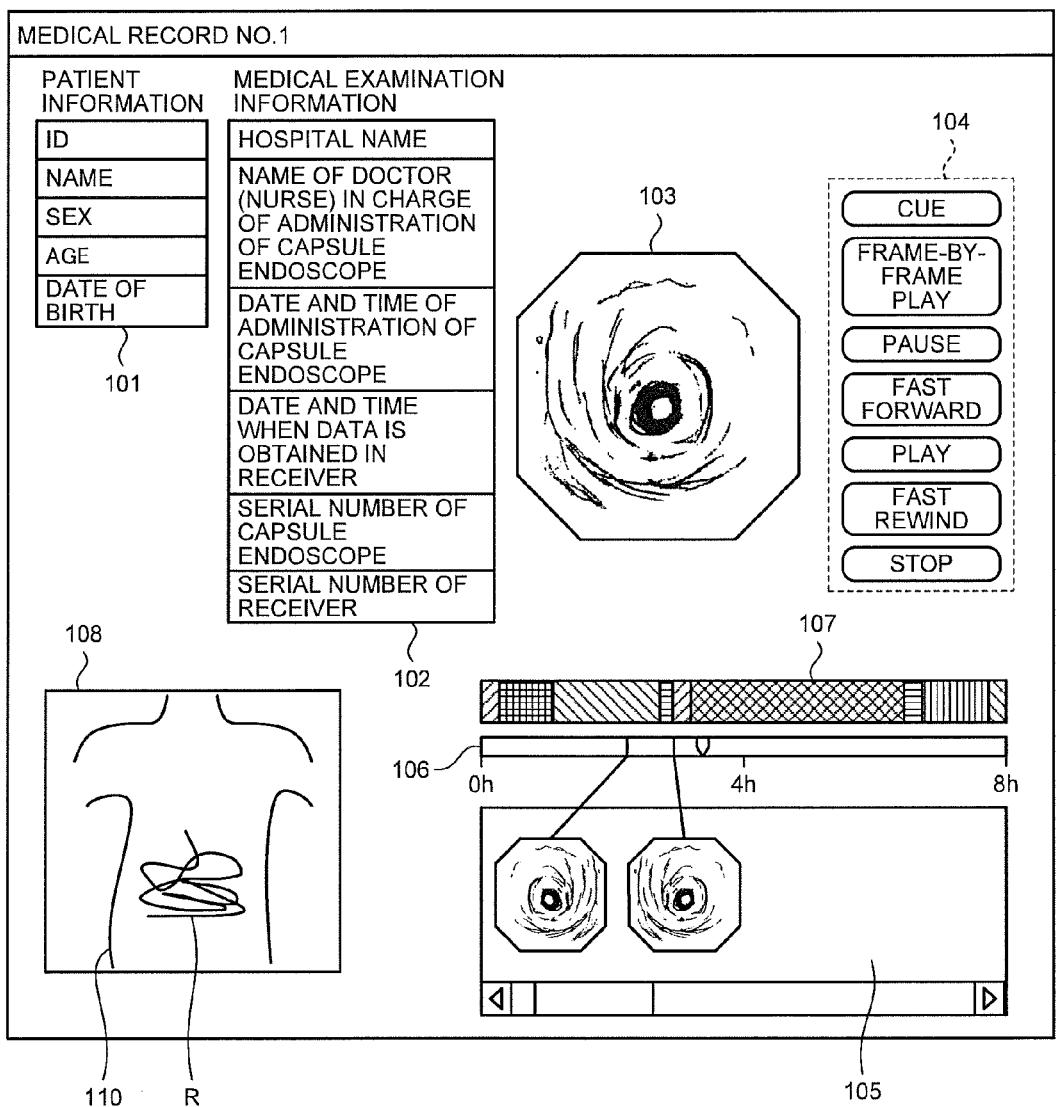
FIG. 9 shows a frame format of an example of an interpretation screen displayed in the display unit.

FIG. 9 shows a frame format of an example of an interpretation screen displayed in the display unit 61. An interpretation screen 100 includes a patient information area 101 in which identification information of the subject 10 as a patient is displayed, a medical examination information area 102 in which identification information of medical examinations performed on the subject 10 is displayed, a main display area 103 in which a series of in-vivo images are reproduced as pseudo moving or still images, a reproducing operation button group 104 which enables an operation of reproducing in-vivo the images displayed in the main display area 103, a thumbnail area 105 in which a plurality of reduced in-vivo images are displayed as thumbnails, a time bar 106 which indicates a time when the in-vivo image currently displayed in the main display area 103 is obtained, a color bar 107 which indicates an average color of each image in the series of in-vivo images in time series, and a track display area 108. The reduced images in the thumbnail area 105 and points on the time bar 106 indicating respective time points when the reduced images are obtained are displayed by being connected by lines in the screen. In a display area at each time point on the color bar 107, an average color of an in-vivo image of the subject captured at each time point is indicated. Here, since each of the series of in-vivo images presents a specific average color depending on the organ captured, it is possible for the interpreter to easily tell the organ shown in an in-vivo image at each time point based on a transition of the average colors along the time axis. In the track display area 108, the track R calculated by the track calculator 57 is displayed by overlapping with a subject image 110 indicating the subject 10.

It is preferable in displaying the interpretation screen 100 that the display controller 60 thins out and displays a group of in-vivo images whose imaging positions are close to each other and which are specified (flag-set) by the specifying unit 55b. Or, only one of a group of in-vivo images whose imaging positions are the same may be displayed. In either case, it is possible to make a rate in displaying a pseudo moving in the main display area 103 high. In the case of displaying in-vivo images as still images, it is possible to reduce the number of in-vivo images to be displayed.

Besides, it is preferable as for the reduced images which are connected to the time bar 106 by lines and displayed in the thumbnail area 105, too that a group of in-vivo images whose imaging positions are close to each other or the same is thinned out or omitted in displaying.

Alternatively, a distance bar may be generated based on in-vivo images after the sorting sequence is changed (after the group of in-vivo images whose imaging positions are close to each other or the same is thinned out and the like as appropriate) and may be displayed together with or instead of the color bar 107 on the interpretation screen 100. Here, the distance bar is generated by one-dimensionally presenting average colors of respective in-vivo images along the sorting sequence of the in-vivo images. In the distance bar, a redundant distance added due to the reciprocatory motion and the like of the capsule endoscope 2 is eliminated. Therefore, it is possible for the interpreter to easily tell the organ shown in each in-vivo image, judging from the transition of the average colors along the corrected track of the capsule endoscope 2.

In addition, a motion detecting process may be performed between each in-vivo image and its previous in-vivo image in the sorting sequence and the rate in displaying a pseudo moving may be automatically adjusted based on a motion amount (magnitude of motion vector) therebetween. For example, a displaying rate is lowered with respect to an in-vivo image having a large motion amount and heightened with respect to an in-vivo image having a small motion amount, so that interpretation efficiency can be improved. The motion detecting process in this case may be performed between in-vivo images whose sorting sequence is not yet changed (i.e., between in-vivo images sorted in the imaging time sequence) or between in-vivo images whose sorting sequence is already changed (i.e., between in-vivo images sorted in the corrected track sequence).

As explained so far, it becomes possible according to the first embodiment to reduce an influence of a reciprocatory motion and the like of the capsule endoscope 2 and to display in-vivo images along a route from an upper to a lower stream in the digestive canal since the sorting sequence of the in-vivo images is changed based on positional information and degree of correlation of the in-vivo images. Besides, since a track of the capsule endoscope 2 is generated according to the changed sorting sequence, it becomes possible to grasp the position indicated by each in-vivo image in the inside of the subject 10 more accurately.

Moreover, it becomes possible to reduce a burden on the interpreter and improve interpretation efficiency in the case of thinning out and displaying a group of in-vivo images whose imaging positions are close to each other or the same.

Modification

There is a situation where the capsule endoscope 2 retains at a position and performs a rotational motion in the inside of the subject 10. In this situation, the check of in-vivo images according to the flowchart shown in FIG. 6 results in a low degree of correlation ("No" at step S122) between the in-vivo image as the check target and the in-vivo image as the comparison target while an already-checked in-vivo image is present around ("Yes" at step S112). To perform an appropriate detection in such a situation, it is only necessary to calculate a degree of correlation after rotating one of the in-vivo images at step S121. It is only necessary to determine a rotation angle on this occasion, by obtaining orientation (rotation angle) information of the capsule endoscope 2 as information related to the in-vivo image data, based on the obtained information. The orientation information of the capsule endoscope 2 can be obtained by using various known methods including a method of providing a magnet in an eccentrically-located manner with respect to a rotation axis and detecting a magnetic field formed by this magnet, for example. When a determination that the degree of correlation is high between both in-vivo images is obtained as a result ("Yes" at step S122), it is only necessary to treat these in-vivo images as a group of in-vivo images whose imaging positions are close to each other or the same.

Second Embodiment

Figure 10:
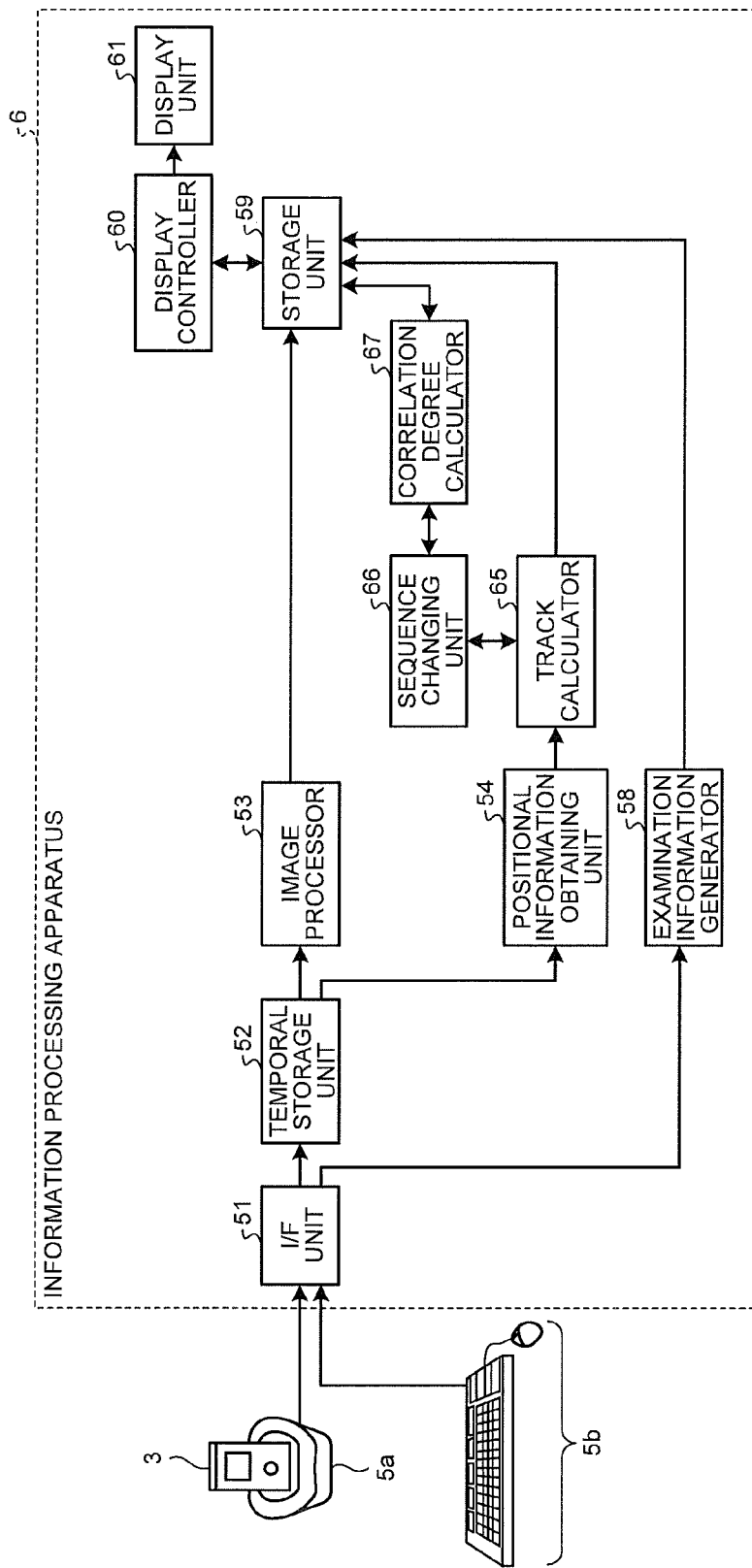
FIG. 10 is a block diagram of a configuration of an information processing apparatus according to a second embodiment of the present invention.

A capsule endoscope system according to a second embodiment will be explained next. A capsule endoscope system according to the second embodiment is provided with an information processing apparatus 6 shown in FIG. 10 instead of the information processing apparatus 5 shown in FIG. 4. The information processing apparatus 6 is provided with a track calculator 65, a sequence changing unit 66, and a correlation degree calculator 67 instead of the sequence changing unit 55, the correlation degree calculator 56, and the track calculator 57 shown in FIG. 4. Other components are the same as those shown in FIGS. 1 to 4.

The track calculator 65 calculates a track of the capsule endoscope 2 in the inside of the subject 10 based on the positional information obtained by the position information obtaining unit 54 and also corrects the track according to the in-vivo image sorting sequence changed by the sequence changing unit 66 to be described later.

The sequence changing unit 66 changes the sorting sequence of the in-vivo images in the initial imaging time sorting sequence based on the positional information obtained by the positional information obtaining unit 54 and a degree of correlation calculated by a correlation degree calculator 67 to be described later.

The correlation degree calculator 67 calculates a degree of correlation between the in-vivo images which are each the determination target on the sorting sequence changed by the sequence changing unit 66.

Figure 11:
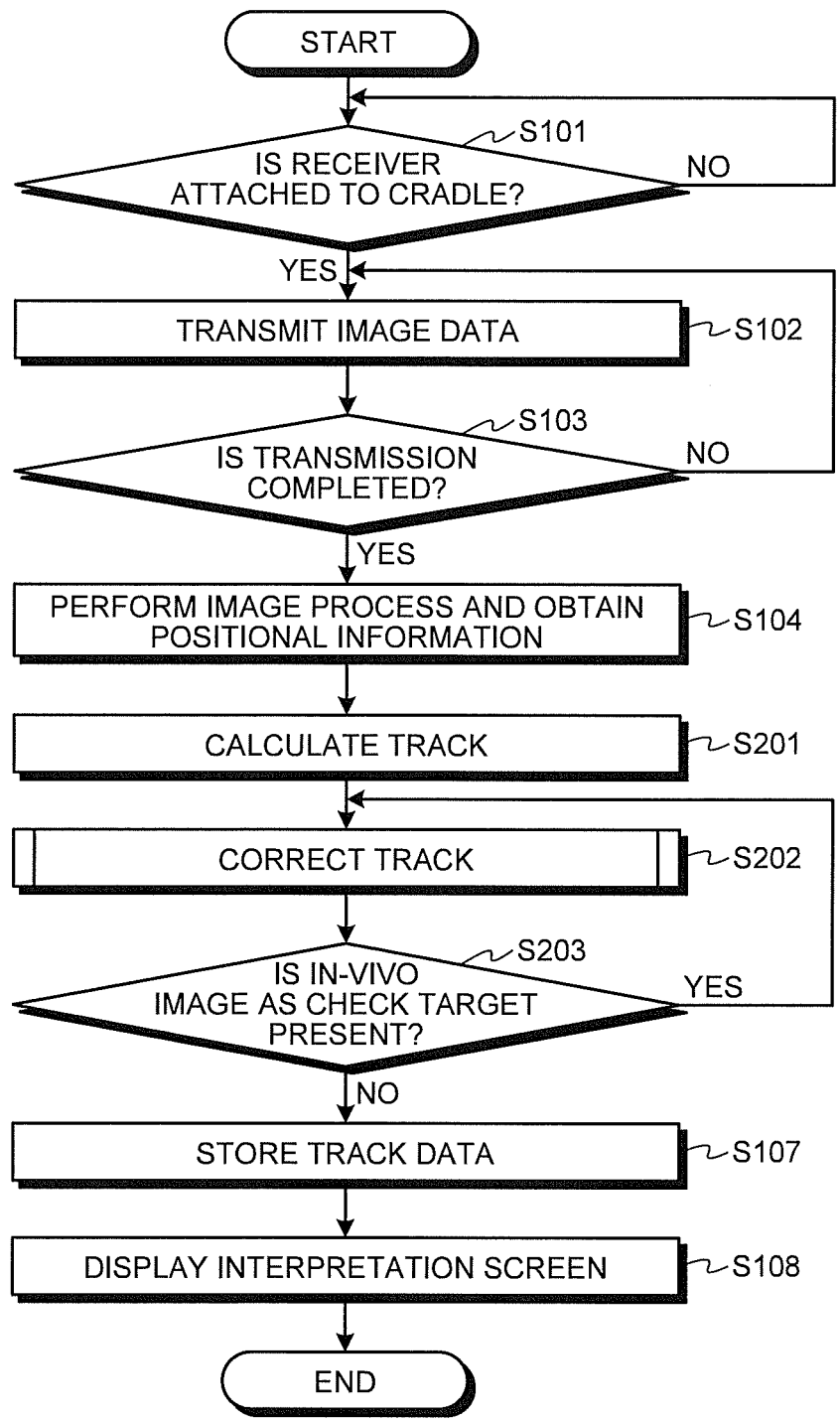
FIG. 11 is a flowchart showing an operation of the information processing apparatus shown in FIG. 10.

FIG. 11 is a flowchart showing an operation of the information processing apparatus 6. In the second embodiment, after the positional information of the series of in-vivo images is obtained by the positional information obtaining unit 54, a track is generated tentatively in the initial sorting sequence (i.e., in the sequence of the imaging time of the in-vivo images) and then corrected by checking each of the in-vivo images and arbitrarily changing the sorting sequence.

At steps S101 to S104 shown in FIG. 11, the information processing apparatus 6 obtains in-vivo image data and its associated information from the receiver 3 and obtains the positional information of the in-vivo images. The detail of these steps is the same as that explained in the first embodiment.

At subsequent step S201, the track calculator 65 calculates a track of the capsule endoscope 2 by sequentially joining respective positions of the in-vivo images in the imaging time sequence. The display controller 60 may control the display unit 61 to display the track tentatively in the interpretation screen based on track data calculated at this stage. In other words, a track correcting process to be explained below is performed in the background while displaying the interpretation screen.

At step S202, the information processing apparatus 6 corrects the tentative track calculated at step S201 by checking positional relation and the like of the in-vivo images. This process is repetitively performed as far as an in-vivo image as a check target is present ("Yes" at step S203).

At step S203, when no more in-vivo image as a check target is present ("No" at step S203), the storage unit 59 stores data of the already-corrected track calculated by the track calculator 65 (step S107). The operation following this step is the same as that in the first embodiment.

Figure 12:
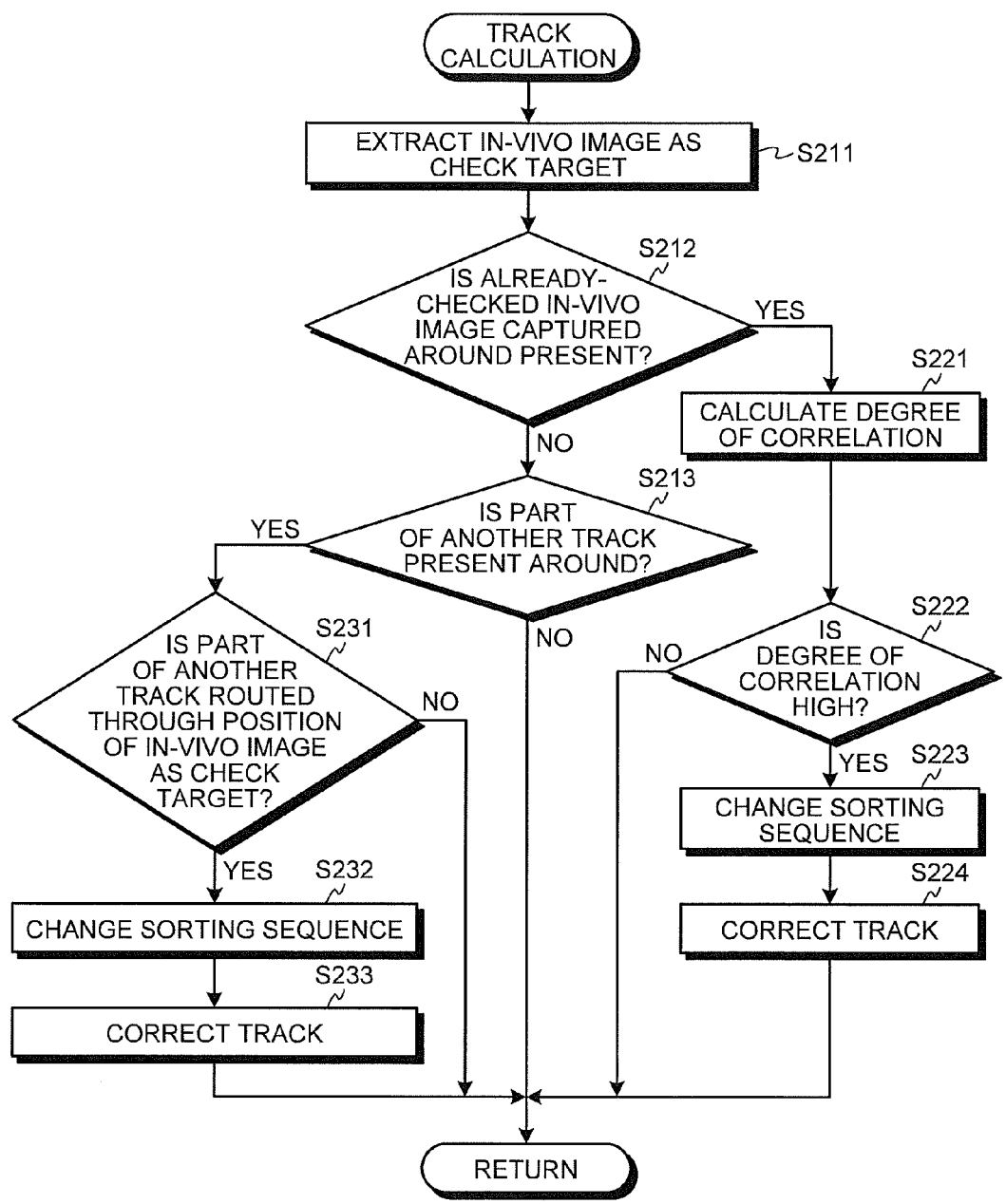
FIG. 12 is a flowchart of a track correcting process executed by the image processing apparatus shown in FIG. 10.
Figure 13A:
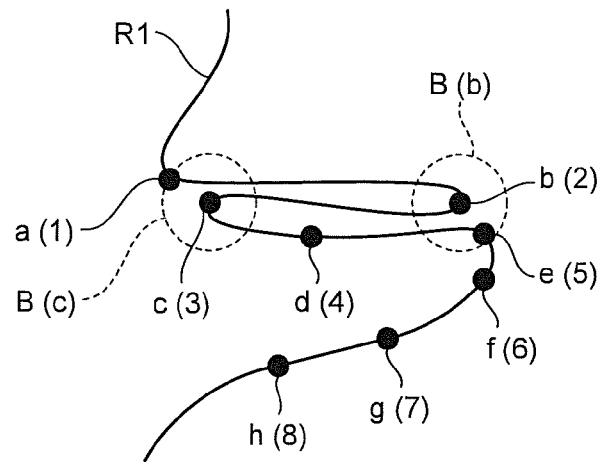
FIGS. 13A to 13C are explanatory views of the track correcting process.
Figure 13B:
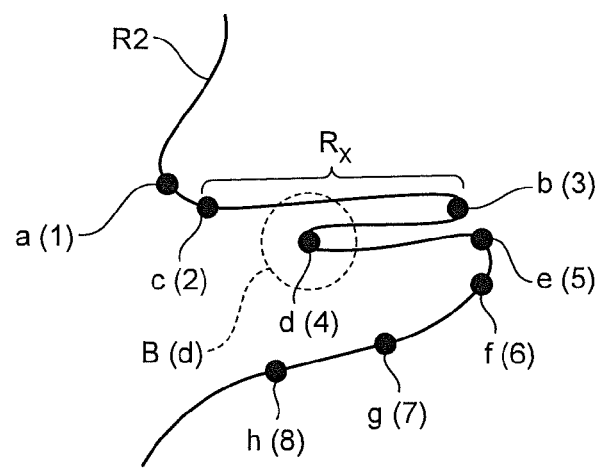
Figure 13C:
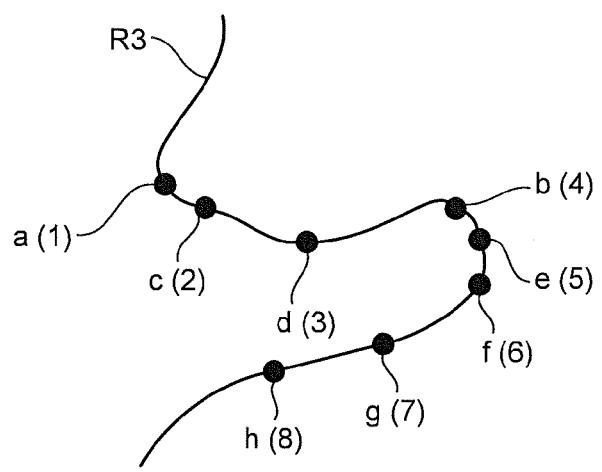

Next, a track correcting process at step S202 will be explained with reference to FIGS. 12 to 13C. FIG. 12 is a flowchart of a track correcting process performed by the image processing apparatus 6. FIGS. 13A to 13C are explanatory views of the track correcting process. In FIGS. 13A to 13C, points a to h which indicate respective positions of the in-vivo images and a tentative track R1 passing through the points a to h are shown. Parenthetic numerals (1) to (8) provided to the points a to h indicate the sorting sequence of the in-vivo images at the respective points a to h.

First at step S211, the sequence changing unit 66 extracts an in-vivo image as a check target and obtains positional information including a positional coordinate of the in-vivo image. The second embodiment is configured to perform the check, since the in-vivo image (sorting sequence 1) at the point a is already checked, along the initial sorting sequence from (2) to (8), starting from the in-vivo image (the sorting sequence 2) at the point b captured right after the in-vivo image (at the sequence 1).

At step S212, the sequence changing unit 66 determines whether or not an already-checked in-vivo image captured around the in-vivo image as the check target is present. Specifically, whether or not a positional coordinate of an already-checked in-vivo image is present within a predetermined range centering around the positional coordinate of the in-vivo image as the check target (within a cube whose side has a predetermined length or within a sphere having a predetermined radius, for example) is determined. For example, when the point b shown in FIG. 13A is checked, no already-checked in-vivo image is present within a predetermined range B(b). When no already-checked point is present within the predetermined range in this situation ("No" at step S212), the operation moves to step S213.

At step S213, the sequence changing unit 66 determines whether or not a part of another track at least one end of which is at a position of an already-checked in-vivo image is present around the in-vivo image as the check target except for a part of the track whose one end is at the position of the in-vivo image as the check target. Specifically, whether or not a part of another track at least one end of which is at a position of an already-checked in-vivo image (hereinafter referred to as simply "another track part") passes through the predetermined range of the position of the in-vivo image as the check target is determined. When the point b shown in FIG. 13A is checked for example, no part of another track passing through the predetermined range B(b) is present. When no part of another track passing through the predetermined range is present in this situation ("No" at step S213), the operation returns to the main routine without making any track correction.

Next, a process in the case where an already-checked in-vivo image captured around the in-vivo image as the check target is present at step S212 ("Yes" at step S212) will be explained. For example, when the point c shown in FIG. 13A is checked, it is found that the point a is included within a predetermined range B(c).

In this case, the correlation degree calculator 67 calculates a degree of correlation between the in-vivo image as the check target and the in-vivo image captured in the vicinity (in-vivo image as a comparison target) (step S221). The index used as the degree of correlation and the determining method are the same as those explained at step S121 (see FIG. 6) in the first embodiment.

When the degree of correlation between in-vivo images is determined to be high ("Yes" at step S222), the sequence changing unit 66 changes the sorting sequence of the in-vivo images based on the positional information of the in-vivo image as the check target, the in-vivo image as the comparison target, and an in-vivo image right before or after the comparison target (step S223). On this occasion, the sequence changing unit 66 may specify a group of in-vivo images whose imaging positions are close to each other and a group of in-vivo images whose imaging positions are the same and may set a flag in in-vivo image data so that they can be treated as in-vivo images belonging to the same group. On the other hand, when the degree of correlation between in-vivo images is determined not to be high ("No" at step S222), the operation returns to the main routine without making any track correction.

When the degree of correlation between the in-vivo image (check target) at the point c and the in-vivo image (comparison target) at the point a is determined to be high, for example, the sequence changing unit 66 extracts a point b right after the point a and changes the sorting sequence so that a route joining these three points becomes the shortest. Thus, the initial sorting sequence "the point a(1)→the point b(2)→the point c(3)" is changed to the sequence "the point a(1)→the point c(2)→the point b(3)" as shown in FIG. 13B.

At subsequent step S224, the track calculator 65 corrects the track based on the changed sorting sequence. Thus, a track R2 in which a part joining the point a and the point b is deleted and a part joining the point a, the point c, and the point b in this order is added instead is generated.

Next at step S213, a process in the case where a part of another track is present around the in-vivo image as the check target ("Yes" at step S213) will be explained. For example, a part $R_x$ of a track whose both ends are at the already-checked points c and b passes through a predetermined range B(d) around the point d in FIG. 13B.

In this case, the sequence changing unit 66 determines whether or not the part of the detected track is routed through the position of the in-vivo image as the check target (step S231). The method of this determination is the same as that explained at step S131 (see FIG. 6) in the first embodiment.

When the part of the detected track is determined to be routed through the position of the in-vivo image as the check target ("Yes" at step S231), the sequence changing unit 66 changes the sorting sequence of the in-vivo image as the check target and the in-vivo images at both end points of the detected track part (step S232). When the track part $R_x$ is determined to be routed through the point d in FIG. 13B, for example, the sorting sequence of the in-vivo images is changed to "the point c(2)→the point d(3)→the point b(4)" according to the determination. At subsequent step S233, the track calculator 65 corrects the track according to the new sorting sequence. As a result, a track R3 in which the track part $R_x$ is deleted and a track part joining the point c and the point d is added is obtained as shown in FIG. 13C.

On the other hand, when the detected track part is determined not to be routed through the position of the in-vivo image as the check target ("No" at step S231), the operation returns to the main routine without making any track correction.

The processes shown at steps S211 to S213, S221 to S224, and S231 to S233 are further repeated with respect to the points e to h to generate a corrected track.

According to the second embodiment as explained above, it is possible to display a track in the interpretation screen at an early stage since the track calculation is first performed after the obtainment of positional information. Thus, it becomes possible for the interpreter to promptly start interpretation and improve interpretation efficiency.

As explained above, it becomes possible according to the first and the second embodiments and the modification to reduce an influence of the reciprocatory motion and the like of the capsule endoscope and to generate a group of in-vivo images along a route in the digestive canal since the sorting sequence of the in-vivo images is changed based on positional information and degree of correlation of the in-vivo images.

The embodiments explained above are only exemplary in carrying out the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An information processing apparatus that performs an image process on data of a group of in-vivo images which are obtained from a capsule endoscope that captures in-vivo images of a subject via a receiver that performs a wireless communication with the capsule endoscope and sorted in an imaging time sequence, comprising:
a storage unit that stores the data of the in-vivo images and information which is associated with the data of the in-vivo images and related to a position of the capsule endoscope in an inside of the subject;
a positional information obtaining unit that obtains positional information of the capsule endoscope in capturing the in-vivo images based on the information related to the position, the positional information including a positional coordinate of the capsule endoscope;
a sequence changing unit that changes a sorting sequence of the in-vivo images along a route from an upper to a lower stream in the digestive canal based on the positional information obtained by the positional information obtaining unit; and
a correlation degree calculator that calculates a degree of correlation between predetermined in-vivo images based on the data of the in-vivo images,
wherein the sequence changing unit that changes the sorting sequence of the in-vivo images based on the positional information obtained by the positional information obtaining unit and the degree of correlation calculated by the correlation degree calculator; and
when a position coordinate of an already-checked second in-vivo image is present within a predetermined range of a position coordinate of a first in-vivo image as a check target and a degree of correlation between the first in-vivo image and the second in-vivo image is higher than a criterion, the sequence changing unit changes the sorting sequence of the first and the second in-vivo images and a third in-vivo image sorted one of right before and right after the second in-vivo image.

2. The information processing apparatus according to claim 1, wherein the degree of correlation is determined based on one of a correlation value of a fixed size block, a traveling amount of a template obtained through a block matching method, and a change rate in brightness of in-vivo images.

3. The information processing apparatus according to claim 1, wherein the sequence changing unit changes the sorting sequence so that a route joining position coordinates of the first, the second, and the third in-vivo images becomes shortest.

4. The information processing apparatus according to claim 1, further comprising a display unit that displays the in-vivo images based on the sorting sequence changed by the sequence changing unit.

5. The information processing apparatus according to claim 1, further comprising a track calculator that calculates a track of the capsule endoscope based on the positional information and the sorting sequence of the in-vivo images changed by the sequence changing unit.

6. The information processing apparatus according to claim 5, wherein the track calculator calculates the track of the capsule endoscope based on the position-related information stored in the storage unit and corrects the track according to the sorting sequence changed by the sequence changing unit.

7. The information processing apparatus according to claim 5, wherein the sequence changing unit determines, when a part of the calculated track passes through a predetermined range of a position coordinate of a first in-vivo image as a check target, whether or not the part of the track is routed through the position coordinate of the first in-vivo image based on a second and a third in-vivo images whose respective position coordinates are at respective ends of the part of the track, and changes the sorting sequence of the first, the second, and the third in-vivo images when the part of the track is routed through the position coordinate of the first in-vivo image.

8. The information processing apparatus according to claim 7, wherein the determination is performed based on a traveling vector of a template obtained by one of a degree of similarity between the first in-vivo image and an interpolated image generated based on the second and the third in-vivo images; an optical flow; and a block matching method.

9. The information processing apparatus according to claim 4, wherein the sequence changing unit includes a specifying unit that specifies one of a group of in-vivo images whose imaging positions are close to each other and a group of in-vivo images whose imaging positions are same based on the positional information and the degree of correlation.

10. The information processing apparatus according to claim 9, wherein the display unit thins out and displays a part of the group of in-vivo images specified by the specifying unit.

11. A capsule endoscope system, comprising:
a capsule endoscope that is inserted to an inside of a subject, performs imaging, and generates in-vivo image data which shows in-vivo images of the subject;
a receiver that receives the in-vivo image data generated by the capsule endoscope via a wireless communication; and
an information processing apparatus that performs an image process on the data of a group of the in-vivo images which are obtained from the capsule endoscope via the receiver and sorted in an imaging time sequence, the information processing apparatus including
a storage unit that stores the in-vivo image data and information which is associated with the in-vivo image data and related to a position of the capsule endoscope in the inside of the subject,
a positional information obtaining unit that obtains positional information of the capsule endoscope in capturing the in-vivo images based on the information related to the position, the positional information including a positional coordinate of the capsule endoscope, and
a sequence changing unit that changes a sorting sequence of the in-vivo images along a route from an upper to a lower stream in the digestive canal based on the positional information obtained by the positional information obtaining unit;
a correlation degree calculator that calculates a degree of correlation between predetermined in-vivo images based on the data of the in-vivo images, wherein the sequence changing unit that changes the sorting sequence of the in-vivo images based on the positional information obtained by the positional information obtaining unit and the degree of correlation calculated by the correlation degree calculator; and when a position coordinate of an already-checked second in-vivo image is present within a predetermined range of a position coordinate of a first in-vivo image as a check target and a degree of correlation between the first in-vivo image and the second in-vivo image is higher than a criterion, the sequence changing unit changes the sorting sequence of the first and the second in-vivo images and a third in-vivo image sorted one of right before and right after the second in-vivo image.

* * * * *